United States Patent [19]

DeLuca et al.

[11] 4,305,880

[45] Dec. 15, 1981

[54] PROCESS FOR PREPARING 24-FLUORO-25-HYDROXYCHOLECALCIFEROL

[75] Inventors: Hector F. DeLuca; Yoko Tanaka, both of Madison, Wis.; Nobuo Ikekawa, Musashinoshi; Yoshiro Kobayashi, Tokyo, both of Japan

[73] Assignee: Wisconsin Alumni Research Foundation, Madison, Wis.

[21] Appl. No.: 189,513

[22] Filed: Sep. 22, 1980

[51] Int. Cl.$^3$ ................................................ C07J 9/00
[52] U.S. Cl. ............................. 260/397.1; 260/397.2; 260/239.55 R
[58] Field of Search ........................... 260/397.1, 397.2

[56] References Cited

U.S. PATENT DOCUMENTS 4,226,788  10/1980  DeLuca et al. .................. 260/397.2

Primary Examiner—Elbert L. Roberts
Attorney, Agent, or Firm—Howard W. Bremer

[57] ABSTRACT

The invention provides a new derivative of vitamin $D_3$, 24-fluoro-25-hydroxycholecalciferol.

The compound is characterized by vitamin D-like activity in its ability to increase intestinal calcium transport, increase serum calcium and inorganic phosphorous concentration and to prevent the development of rickets. It would find ready application as a substitute for vitamin $D_3$ and in the treatment of disease states evincing calcium-phosphorous imbalance and which are non-responsive to vitamin $D_3$ therapy.

6 Claims, No Drawings

PROCESS FOR PREPARING 24-FLUORO-25-HYDROXYCHOLECALCIFEROL

The invention described herein was made in the course of work under a grant or award from the Department of Health and Human Services, and U.S. Japan Cooperative Grant INT-76-05793 and IPA No. 0001 awarded by the National Science Foundation.

TECHNICAL FIELD

This invention relates to a compound which is characterized by vitamin D-like activity.

More specifically this invention relates to a method for preparing a derivative of vitamin $D_3$ and the new and novel intermediates in such process.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective vitamin $D_3$ must be converted in vivo to its hydroxylated forms. For example, the vitamin $D_3$ is first hydroxylated in the liver to form 25-hydroxy vitamin $D_3$ and is further hydroxylated in the kidney to produce $1\alpha,25$-dihydroxyvitamin $D_3$ or $24,25$-dihydroxy vitamin $D_3$. The $1\alpha$-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

BACKGROUND ART

References to various of vitamin D derivatives are extant in the patent and other literature. See, for example, U.S. Pat. Nos. 3,565,924 directed to 25-hydroxycholecalciferol; 3,697,559 directed to 1,25-dihydroxycholecalciferol; 3,741,996 directed to $1\alpha$-hydroxycholecalciferol; 3,907,843 directed to $1\alpha$-hydroxyergocalciferol; 3,715,374 directed to 24,25-dihydroxycholecalciferol; 3,739,001 directed to 25,26-dihydroxycholecalciferol; 3,786,062 directed to 22-dehydro-25-hydroxycholecalciferol; 3,847,955 directed to 1,24,25-trihydroxycholecalciferol, 3,906,014 directed to 3-deoxy-$1\alpha$-hydroxycholecalciferol; 4,069,321 directed to the preparation of various side chain fluorinated vitamin $D_3$ derivatives and side chain fluorinated dihydrotachysterol$_3$ analogs; 4,188,345 directed to a process for preparing fluorinated vitamin D compounds; 4,196,133 directed to 24,24-difluoro-25-hydroxycholecalciferol.

DISCLOSURE OF INVENTION

A new method for preparing 24-fluoro-25-hydroxycholecalciferol (24-fluoro-25-hydroxyvitamin $D_3$ or 24-F-25-OH-$D_3$) has now been found by which said compound can be readily prepared. 24-F-25-OH-$D_3$ expresses excellent vitamin D-like activity as measured by its ability to stimulate calcium transport in intestine and its ability to increase serum calcium concentration. Such compound, therefore, could serve as a substitute for vitamin D in its various metabolic bone diseases such as osteomalacia, osteodystrophy and hypoparathyroidism.

BEST MODE FOR CARRYING OUT THE INVENTION

24-F-25-OH-$D_3$ was synthesized in accordance with the following description and abbreviated schematic:

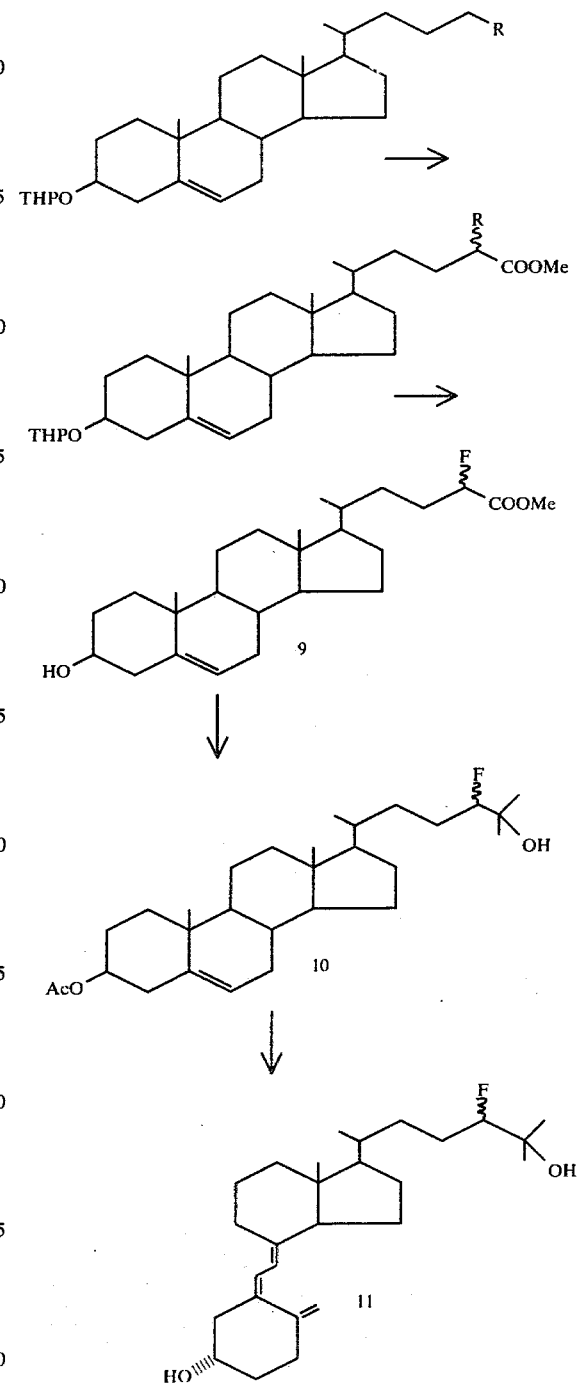

1 R OTs
2 R CN
3 R COOH
4 R COOMe
5 R I
6 R OH
7 R OTs
8 R F

SYNTHESIS of 24-FLUORO-25-HYDROXYCHOLECALCIFEROL

For the synthesis of 24F-25-hydroxyvitamin $D_3$ 11, cholenic acid is successively treated with dihydropyran-p-TsOH, $LiAlH_4$, and p-TsCl-pyridine to afford the tosylate 1, which in turn is reacted with KCN/18-crown-6 in dimethylformamide at 70° C. for 3 hr. to give the cyanide 2 (48% yield, mp 142-143). Hydrolysis of 2 with KOH in aqueous ethanol (140°, 48 hr.) yielded the carboxylic acid 3 (63% yield, mp. 171°-172° C.), which on treatment with $CH_2N_2$ gives the methyl ester 4 (79% yield, mp 159°-161°). The enolate of 4 (generated by treatment with lithium dicyclohexylamide at −78° C.) was treated with iodine in THF at −78° C. to yield the idodide 5. Substitution of iodine of 5 with hydroxyl was accomplished by reaction with $CF_3COOAg-Ag_2O$ in $CH_3CN$-ethyl ether (20° C., 16 hr.). Reesterification with $CH_2N_2$ gave the hydroxy ester 6 (mp 114°-117° C., $\delta 4.16$ (1H, m, C-24), m/e 418 (M-84)) in 63% overall yield from 4. (The 3,24-dibenzoyl ester derived from 6 showed a twin peak on high pressure liquid chromatography (HPLC) (Zorbax-SIL, 10% $CH_2Cl_2$ in n-hexane), indicating that 6 is a 1:1 epimeric mixture at C-24 position. This was further corroborated by transformation of 6 into a 1:1 mixture of (24R)- and (24S)-3,24-dibenzoyloxycholest-5-ene-25-ol trimethylsilyl ether which was cochromatographed on HPLC with authentic samples (M. Seki, N. Koizumi, M. Morisaki and N. Ikekawa, Tetrahedron Letters, 15 (1973)).)

The tosylate 7 derived from 6 was treated with KF/18-crown-6 in dimethylformamide (70° C., 15 hr.) to give the fluoride 8, which on hydrolysis (p-TsOH in methanol-$CH_2Cl_2$, 0°, 4 hr.) affords the fluoro ester 9 (73% yield, mp 104°-105° C. $\delta 4.86$ (1H, dm, $J_{hf}=48$ Hz, C-24), m/e 420 (M+)). Treatment of 9, which if desired can be reprotected at $C_3$ by acylation (e.g. acetylation, benzoylation) by known procedures, with an excess of $CH_3MgI$ in ethyl ether (20° C., 20 min) followed by acetylation furnished in 80% yield, the fluorohydrin 10 (mp 153°-154° C., $\delta 4.14$ (1H, dm, $J_{Hf}=48$ Hz, C-24), 1.20 (6H, S, C-26,27), m/e 402 (M-60)). Conversion of 10 to the corresponding vitamin $D_3$ 11 was carried out essentially as described for 24,24-difluoro-25-hydroxycholecalciferol in U.S. Pat. No. 4,196,133, issued Apr. 1, 1980 and in Y. Kobayashi, T. Taguchi, T. Terada, J. Oshida, M. Morisaki and N. Ikekawa. Synthesis of 24,24-difluoro and 24-fluoro-25-hydroxyvitamin $D_3$. Tetrahedron Letters, No. 22, pp. 2020 (1979).

Compound 11 showed the expected spectral properties ($\lambda_{max}$ 263, nm, $\lambda_{min}$ 228, nm, m/e 418 (M+), 402 (M-15), 400 (M-18), 385 (M-15-18), 359, 271, 253, 136, 118).

BIOLOGICAL ACTIVITY

Male weanling rats were purchased from Holtzman Company, Madison, Wis., were housed in hanging wire cages and were fed ad libitum water and the low calcium vitamin D-deficient diet as described by Suda et al. (J. Nutrition 100, 1049, 1979) for three weeks prior to their use in the following assays.

INTESTINAL CALCIUM TRANSPORT

Rats that had been fed the low-calcium, vitamin D-deficient diet described above were divided into three groups of 5 rats each. The rats in each group were then respectively given a single dose of 650 pmole of either 24-F-25-OH-$D_3$ or 25-OH-$D_3$ dissolved in 0.1 ml 95% ethanol intrajugularly 23 hours prior to sacrifice. Rats in the control groups were given the ethanol vehicle only in the same manner. The rats in the groups were killed by decapitation and their blood was collected for the measurement of serum calcium concentration. Their duodena were used to measure intestinal calcium transport activity in accordance with the technique of Martin and DeLuca (Am. J. Physiol. 216, 1351, 1969) with the results shown in Table I, second column.

SERUM CALCIUM CONCENTRATION

The blood collected as described above was centrifuged to obtain the serum. One-tenth ml of serum was mixed with 1.9 ml of 0.1% lathanum chloride solution and the calcium concentration was measured with an atomic absorption spectrophotometer (Perkin-Elmer Model HO-214). Results are shown in Table 1, third column.

It is evident from Table I, that 24-fluoro-25-hydroxyvitamin $D_3$ exhibits pronounced vitamin D-like activity as evidenced by the increase of intestinal calcium transport and increase in the concentration of serum calcium and appears to be wholly as effective in this regard as 25-hydroxyvitamin $D_3$ (see U.S. Pat. No. 3,565,924).

TABLE I

Intestinal Calcium Transport and Increase in Serum Calcium Concentration in Response to a Single Dose of 650 pmole 24-F-25-OH—$D_3$ or 25-OH—$D_3$ Given 24 hrs. Prior to Sacrifice.

| Compound Given | Intestinal Calcium Transport $^{45}$Ca serosal/$^{45}$Ca mucosal | Serum Calcium mg/100 ml |
|---|---|---|
| ethanol (control) | 1.5 ± 0.4*[a] | 5.0 ± 1.1[d] |
| 24-F-25-OH—$D_3$ | 3.7 ± 0.5[b] | 8.4 ± 0.4[e] |
| 25-OH—$D_3$ | 4.5 ± 0.8[c] | 7.7 ± 0.4[f] |

*Standard deviation of the mean. Significance of difference:
[b] & [c] from [a] p<0.001
[b] from [c] N.S.
[e] from [d] p<0.001
[f] from [d] p<0.005
[e] from [f] p<0.05

What is claimed is:
1. 24-fluoro-25-hydroxycholecalciferol.
2. 24-fluoro-25-hydroxy previtamin $D_3$.
3. Compounds having the formula

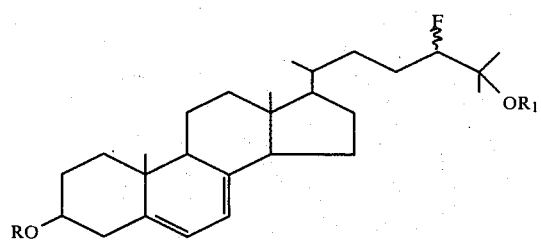

where each of R and $R_1$ is hydrogen or acetyl.
4. Compounds having the formula

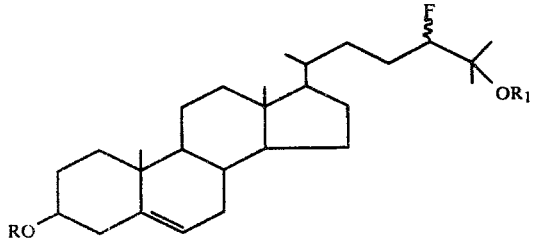

where each of R and $R_1$ is acetyl or hydrogen.

5. Compounds having the formula

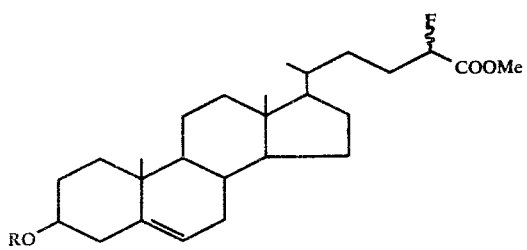

where R is tetrahydropyranyl, hydrogen, or acyl.

6. A method for preparing 24-fluoro-25-hydroxy-cholecalciferol which comprises:

converting 3-tetrahydropyranyl homocholenic acid ester to its enolate by treatment with lithium dicyclohexylamide and treating the enolate with iodine whereby 3-tetrahydropyranyl-24-iodo-homocholenic acid ester is obtained converting said 24-iodo-homocolenic acid ester to 3-tetrahydropyranyloxy-24-hydroxy homocholenic acid by treatment with $CF_3$ $COORA$-$g$—$Ag_2O$ reesterifying said 3-tetrahydropyranyloxy-24-hydroxy homocholenic acid with diazomethane to obtain 3-tetrahydropyranyloxy-24-hydroxy homocholenic acid methyl ester and converting said ester to 3-tetrahydropyranyloxy-24-tosyloxy-homocholenic acid methyl ester treating said tosylate with potassium fluoride to obtain 3-tetrahydropyranyloxy-24-fluoro-homocholenic acid methyl ester hydrolyzing said 3-tetrahydropyranyloxy-24-fluoro-homocholenic acid methyl ester to obtain 24-fluoro-homocholenic acid methyl ester treating said ester with a Grignard reagent followed by acetylation to produce 24-fluoro-25-hydroxy-cholesterol 3-acetate allylically brominating said cholesterol acetate followed by dehydrobromination and separating 3-acetoxy-24-fluoro-25-hydroxy-5,7-cholestadiene saponifying said diene and exposing the resulting 3,25-dihydroxy-24-fluoro-5,7-cholestadiene to actinic radiation whereby 24-fluoro-25-hydroxy previtamin $D_3$ is obtained thermally isomerizing said previtamin and recovering 24-fluoro-25-hydroxy-cholecalciferol.

* * * * *